(12) United States Patent
Townsend et al.

(10) Patent No.: US 12,201,606 B2
(45) Date of Patent: Jan. 21, 2025

(54) CANNABIS PRODUCT

(71) Applicant: 1091665 B.C. Ltd., Sooke (CA)

(72) Inventors: Deryl Townsend, Sooke (CA); Haydn Wilford, Campbell River (CA); Ian Hillier-Brook, Sooke (CA)

(73) Assignee: 1091665 B.C. Ltd., Sooke (CA)

( * ) Notice: Subject to any disclaimer, the term of this patent is extended or adjusted under 35 U.S.C. 154(b) by 808 days.

(21) Appl. No.: 17/313,734

(22) Filed: May 6, 2021

(65) Prior Publication Data

US 2021/0267935 A1 Sep. 2, 2021

Related U.S. Application Data

(62) Division of application No. 15/886,740, filed on Feb. 1, 2018, now Pat. No. 11,026,915.

(60) Provisional application No. 62/489,273, filed on Apr. 24, 2017.

(51) Int. Cl.
| | | |
|---|---|---|
| *A61K 31/352* | (2006.01) | |
| *A24F 40/10* | (2020.01) | |
| *A24F 40/42* | (2020.01) | |
| *A61K 9/00* | (2006.01) | |
| *A61K 36/185* | (2006.01) | |
| *A61K 47/10* | (2017.01) | |

(52) U.S. Cl.
CPC ............ *A61K 31/352* (2013.01); *A24F 40/42* (2020.01); *A61K 9/007* (2013.01); *A61K 36/185* (2013.01); *A61K 47/10* (2013.01); *A24F 40/10* (2020.01)

(58) Field of Classification Search
None
See application file for complete search history.

(56) References Cited

FOREIGN PATENT DOCUMENTS

| CA | 3000295 A1 | 4/2017 |
|---|---|---|
| GB | 2392093 | 2/2004 |

OTHER PUBLICATIONS

Giroud et al., E-Cigarettes: A Review of New Trends in Cannabis Use, Int. J. Environ. Res. Public Health 2015, 12, 9988-10008. (Year: 2015).

*Primary Examiner* — Michael V Meller
(74) *Attorney, Agent, or Firm* — Bennett Jones LLP

(57) ABSTRACT

The present invention comprises a method of manufacturing a cannabinoid solution including adding to a cannabis source comprising a cannabis distillate or a full spectrum alcohol extracted cannabis oil, adding a PEG, forming a mixture; and adding a PG to the mixture, forming the cannabinoid solution suitable for vaporization and inhalation to administer active cannabis compounds to a person in need thereof.

6 Claims, 2 Drawing Sheets

CANNABIS PRODUCT

CROSS REFERENCE

This application is a divisional application from U.S. Ser. No. 15/886,740, filed Feb. 1, 2018 and priority is claimed from the provisional patent application 62/489,273, filed Apr. 24, 2017.

FIELD

This invention relates to a method and product for the administration of cannabis. More particularly, this invention relates to administration of vaporized cannabis.

BACKGROUND

Methods and products for vaporization of nicotine are known in the art. Several patents have been issued for nicotine vaporization apparatuses and methods of delivery of nicotine vapor into the bloodstream.

Cannabis is a well-known pharmacologically active compound that may provide numerous benefits. Several medicinal uses have been found for the active ingredients of cannabis, including tetrahydrocannabinol (THC), cannabinol (CBN), cannabidiol (CBD) and cannabichromene (CBC), commonly referred to as cannabinoids. The medicinal uses of cannabis may include:
- treatment of nausea and pain associated with cancer and chemotherapy;
- nausea associated with aids;
- arthritis and rheumatism;
- glaucoma;
- sleeplessness;
- stomach cramps;
- migraines;
- muscle spasticity associated with multiple sclerosis and paralysis;
- alcohol and narcotic withdrawal;
- stress and depression;
- asthma; and
- epileptic seizures.

Cannabis may be consumed by smoking. Combustion of cannabis may release toxic carcinogens such as ammonia and hydrogen cyanide as well as tar. Moreover, the physiological and pharmacological effects of cannabis may depend on a number of factors including the method of administration.

Cannabis may also be consumed by vaping. Existing vaping fluids, such as EJMIX™, Dat Special Sauce™, etc. are known for vaping THC. These products rely on an end user to dilute a cannabis concentrate with their product. However the following problems may be associated with use of these products:
- fat or wax separation due to insolubility in PG/PEG;
- inconsistent potency of cannabis;
- inconsistent taste due to the terpene content in the cannabis concentrate; and
- end users report an unpleasant taste, because no flavoring is added.

Due to the unpleasant taste end users have attempted adding flavored electronic cigarette fluid to a cannabis concentrate. In these instances, there may be a separation of the fluids because the electronic cigarette fluid likely has a high vegetable glycerin content. The separation of the fluids may impair consistent vapor production and more importantly may force the cannabinoid out of the solution, thereby making it difficult to vape the cannabinoid. In addition, separation of the fluids may impair the mechanics and longevity of the wicks and burners of a vaporizer.

SUMMARY OF THE INVENTION

In accordance with a broad aspect of the present invention, there is provided a method for producing a vaporizable cannabinoid solution comprising: adding a cannabis source selected from (i) a cannabis distillate and/or (ii) a full spectrum alcohol extracted cannabis oil to a polyethylene glycol (PEG) to form a mixture; and combining the mixture with a propylene glycol (PG) to form the solution.

In accordance with another broad aspect of the present invention, there is provided a method for producing a vaporizable cannabinoid solution comprising: preparing a solvent extraction of a cannabis starting material; filtering precipitate from the solvent extraction; separating the solvent extraction by distillation to obtain a cannabis distillate containing a cannabinoid; adding the cannabis distillate to a polyethylene glycol (PEG) to form a mixture; and combining the mixture with a propylene glycol (PG) to form the solution.

In accordance with another broad aspect of the present invention, there is provided a pre-packaged cannabis vaporizing fluid comprising: a sealable liquid container; and a vaporizable cannabis solution contained in the sealable liquid container, the composition comprising a cannabis source selected from (i) a cannabis distillate and/or (ii) a full spectrum alcohol extracted cannabis oil; polyethylene glycol (PEG); and propylene glycol (PG).

It is to be understood that other aspects of the present invention will become readily apparent to those skilled in the art from the following detailed description, wherein various embodiments of the invention are shown and described by way of illustration. As will be realized, the invention is capable for other and different embodiments and its several details are capable of modification in various other respects. Accordingly the drawings and detailed description are to be regarded as illustrative in nature and not as restrictive.

DESCRIPTION OF THE FIGURES

For a better appreciation of the invention, the following Figures are appended.

DETAILED DESCRIPTION

Figure 1:
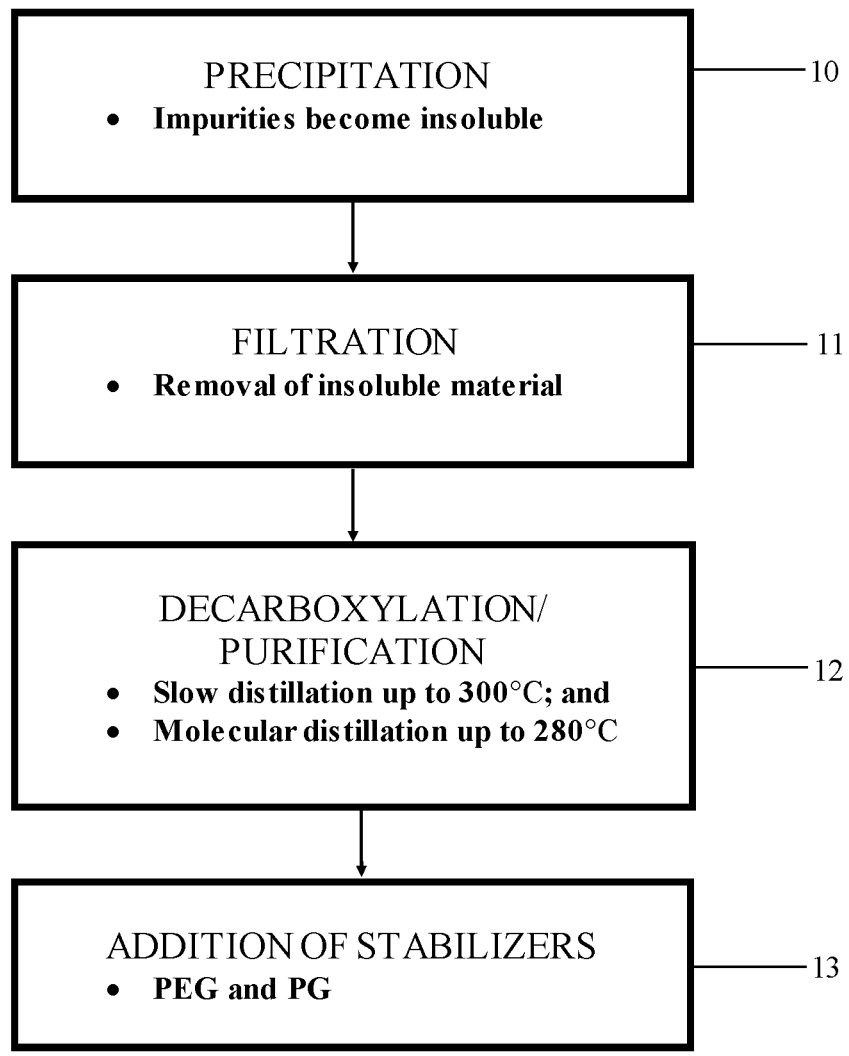
FIG. 1. is a method flow diagram for making a cannabis distillate and producing a vaporizable cannabinoid solution.

The detailed description and examples set forth below are intended as a description of various embodiments of the present invention and are not intended to represent the only embodiments contemplated by the inventor. The detailed description includes specific details for the purpose of providing a comprehensive understanding of the present invention. However, it will be apparent to those skilled in the art that the present invention may be practiced without these specific details.

"Cannabis" refers to plants and all natural and synthetic derivatives of *Cannabis sativa* or *Cannabis indica*. The terms cannabis, cannabis source, cannabis concentrate, cannabis product, cannabinoid, and cannabinoid concentrate, are used herein to refer to physiological active substances derived from the family of cannabis plants, for example

*Cannabis sativa* or *Cannabis indica*, and synthetic cannabis analogues and derivatives, precursors, metabolites or related substances having cannabis-like physiological effects. Common cannabis starting materials include hemp, marijuana or hashish that contain any one or more cannabinoid compound including tetrahydrocannabinol (THC), tetrahydrocannabinol acid (THCA), cannabinol (CBN), cannabidiol (CBD), cannabidiol acid (CBDA), cannabigerolic acid (CBG-A), cannabigerol (CBG) and cannabichromene (CBC).

In one embodiment of the present invention, a cannabinoid concentrate is suspended in an alcohol free vaping solution that is combined with stabilizers; polyethylene glycol (PEG) and propylene glycol (PG). The source of cannabis may be a cannabis distillate or a full spectrum alcohol extracted cannabis oil. The present invention combines a cannabis source with stabilizers to provide a cannabis vaping solution that is easy to use, can be sold premixed with a specified concentration of active ingredient and has a long shelf-life. In one aspect of the present invention, the solution can be premixed and remains mixed and homogeneous unlike some other vaping substances. Dilution of the cannabis source in the stabilizers and premixing permits a solution to be marketed with a known, desired cannabinoid concentration in the solution. A method of manufacturing a vaporizable cannabinoid solution may include adding a cannabis source selected from (i) a cannabis distillate or (ii) a full spectrum alcohol extracted cannabis oil to a PEG to form a mixture; and combining the mixture with a PG to form the solution.

The solution may be free of terpenes and medium chain triglycerides.

In the present invention the cannabis source may be purified by distillation to obtain a cannabis distillate. The distillate may be a high purity cannabis source, whereby the solution comprises of up to 96% of the active pharmacological ingredients, for example THC and/or CBD. Further purification, such as by column chromatography can yield a product with up to 99.9% purity of THC and/or CBD. A method of manufacturing the cannabis distillate is further described below.

In the present invention the cannabis source could be a full spectrum alcohol extracted cannabis oil. A full spectrum alcohol extracted cannabis oil is a combination of cannabinoids, omega fatty acids, lipids, terpenes, and plant matter. Cannabis oil is a thick, sticky and resinous substance made up of cannabinoids, such as THC and CBD that are extracted from the naturally occurring cannabis plants: *Cannabis sativa* or *Cannabis indica*. Cannabis oil is a cannabis based product obtained by separating the resins from cannabis flowers using a solvent extraction process. The cannabis oil is also known as marijuana oil, Rick Simpson Oil (RSO), full extract cannabis oil (FECO), hash oil, dabs, shatter or wax.

In the present invention, polyethylene glycol (PEG) may be added to the cannabis source. PEG is a polyether compound with many applications from industrial manufacturing to medicine. It is also known as polyethylene oxide or polyoxyethylene, depending on its molecular weight. The structure of PEG is commonly expressed as H—(O—CH$_2$—CH$_2$)n-OH. PEG may be prepared by polymerization of ethylene oxide and may be commercially available over a wide range of molecular weights from 300 g/mol to 10,000,000 g/mol. The numbers that are often included in the names of PEG indicate their average molecular weights (i.e. a PEG with n=9 would have an average molecular weight of approximately 400 daltons, and would be labeled PEG 400). PEG with high molecular weights may have different physical properties such as high viscosity due to the chain length. In the present invention the method includes adding to the cannabis oil or distillate a PEG such as PEG 200, 300, 400, 540 or 600, in a about a 1:1 ratio, wherein the ratio range may be 1.5-0.5:1 (V/V) to form a mixture.

In the present invention, propylene glycol (PG) may be added to the above mixture. PG is a synthetic organic compound with the chemical formula $C_3H_8O_2$ and is a viscous and colorless liquid that may be miscible in water. In the present invention, the method comprises combining the mixture with PG in ratio range from 1:200 to 1:1 (volume of mixture:volume of PG) to form a solution suitable for vaping. The solution may be used directly, packaged for sale or for distribution.

Sometimes in order to avoid separation of the fat matter, wax or lipids from solution an additional filtration step may be performed. The filtration of any immiscible matter further improves the homogeneity and clarity of the cannabis product. If a distillate is used as the cannabis source, then it may readily mix with the stabilizers and filtration may not be necessary. If the alcohol extracted cannabis oil is used as the cannabis source, then some of the chemical constituents of the extract may not be soluble in PEG and/or PG and filtration may be necessary. For example, chlorophyll, fatty acids, plant waxes, particulate matter may be immiscible contaminants in the oil that may not dissolve in the solution and may float on top of the solution or stay suspended in the solution for example as an emulsion. This can be avoided by filtration. Upon filtration, the cannabinoids remain in solution and therefore the filtrate is of interest. A homogeneous cannabinoid solution may be achieved by filtering the solution and isolating the filtrate.

As noted above, a distillate may be used as the cannabis source. Using a cannabis distillate may be advantageous as the filtration step may be avoided. Also, because the distillate contains cannabinoids in very high purity, a known amount of active ingredient (i.e. of THC or CBD) is contained in each volume of distillate. In addition, as the amount of active ingredients in the final product is known, fewer adjustments must be made to achieve a desired percent concentration of active ingredients in the solution can be readily determined and specified. For example, if the distillated is determined to have 90% active ingredient, known volumes of distillate added to known volumes of stabilizers permits an accurate cannabinoid concentration in the vaping solution.

As shown in FIG. 1, the method of producing a vaporizable cannabis solution may include: a solvent extraction 10 of a cannabis starting material; filtering 11 a precipitate from the solvent extraction and isolating the filtrate; separating 12 the solvent extraction by distillation to obtain a cannabis distillate containing a cannabinoid; and adding 13 the cannabis distillate stabilizers to form the solution. Adding includes adding the distillate to a volume of PEG to form a mixture and combining the mixture with an amount of PG to form the solution.

Thus, the method of manufacturing a cannabis distillate may include a solvent extraction and precipitation. Precipitation allows for the removal of non-target materials, also referred to as impurities, which may be materials derived from the cannabis starting material that can solidify after cooling the solvent extract. The starting material may be any plant matter that contains cannabinoids that may be extracted, for example, by a solvent. The starting material may include, but is not limited to flowers, trims and/or leaves. Alternately, the starting material may be an amount of processed plant material such as a crude extract for example: Rosin, kief, hashish, cannabis oil, shatter, FECO, $CO_2$, etc.

The solvent extraction may be performed with a solvent capable of solubilizing cannabinoids such as ethanol, methanol, butane, propane, ether, naphtha, acetone or isopropanol. The solvent may be added in an amount in a range from 5:1 to 10:1 (volume to weight of starting material to be dissolved).

The temperature range for the solvent extraction heating step is dependent on the boiling point of the solvent employed. Heating is performed to dissolve all components of the starting material including the impurities. For example with acetone, heating to 35° C. or more would likely dissolve all of the starting material. In one embodiment, the acetone solvent mixture is heated to a temperature range of 36° C. to 50° C. In another embodiment, the acetone solvent mixture is heated to at least 40° C. to 45° C. Heating the starting material in solvent can improve solubility and miscibility of the starting material in the solvent and dissolve the cannabinoids.

The heated mixture may then be chilled to allow precipitation of impurities. The heated mixture may be chilled to a temperature range of −20° C. to −40° C. The heated mixture may be chilled over 12 to 24 hours, up to a maximum of 30 hours. The solvent extraction and precipitation step reduces the impurities in the cannabis extract and may be any treatment that results in the selective removal or reduction of impurities.

Precipitation of insoluble impurities is typically followed by filtration 11. Filtration may be performed using first a coarse filtration membrane, then a fine filtration membrane. For example one or more layers of a 10-30 micron filter may be used as a coarse filtration membrane. Filtration results in a cannabinoid filtrate where solid impurities are selectively removed or reduced therefrom.

The method may further include isolation of a concentrated filtrate, which may be achieved by a multi-step evaporation under reduced pressure, for example by rotary evaporation or other known techniques.

The method may also include purification and/or decarboxylation 12 of the filtrate. THC and CBD are the principle bioactive constituents in cannabis. However, these constituents may be present as biologically inactive carboxylic acids in the cannabis starting material i.e. THCA and CBDA To convert THCA and/or CBDA into their more readily extractable and pharmacologically active forms (i.e. THC and CBD) it may be necessary to perform a decarboxylation step. Over time, THCA and CBDA may slowly decarboxylate. One way to accelerate the rate of decarboxylation is to apply heat. In one embodiment, the filtrate is slowly heated using 1-2° C. increments over a temperature range from 30° C. to 280° C. The distillation fraction of interest, the cannabis distillate, may be isolated at a vapor temperature in the range of 220° C. to 240° C. under a vacuum pressure in the range of 0.1 TORR to 0.3 TORR. This fraction may be collected until there is little or no visible condensate produced at the above-noted temperature range. Distillation provides a further purified and pharmacologically active product, the distillate.

In another step of the method, stabilizers including PEG and PG may be added 13 to the distillate. Stabilizers such as PEG and PG impede the mixture from separating into two or more parts and provide a suitable solution for administration to a person by vaporization and inhalation. The method may include adding to the cannabis distillate a PEG for example PEG 200, 300, 400, 540 or 600, in a ratio range of 3:1 to 1:1 (volume of PEG to cannabinoid weight), thereby forming a mixture. PG may be added to the mixture in a ratio range of 200:1 to 1:1 ratio (volume of PG to mixture), to form the solution.

In another aspect of the invention, additives may be combined with the solution before vaporization to modify the taste and/or smell of the solution. Additives may include flavorings for example mint, strawberry, vanilla, chocolate, berries, etc.

The vaping solution may be loaded into a vapor tank, the vapor tank configured for vaporization with a vaporizer, for example a personal vaping pen or e-cigarette device. Premixed, packaged vaping solution offers ease of distribution and use, while offering control over quality and content. A premixed, packaged vaping solution may be convenient and reliable for end users, distributors and regulators. In one aspect, therefore, the invention relates to a pre-loaded vapor tank.

Figure 2:
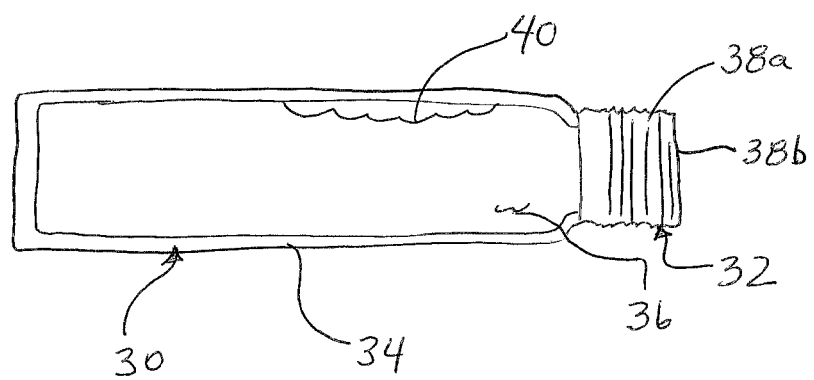
FIG. 2. is a schematic side elevation of a vaporizing tank.

With reference to FIG. 2, for example, a vapor tank may include a tank body 30 and a fitting end 32. The tank body includes a wall 34 that defines within it a chamber 36. Tank body 30 may be formed of a material that reduces passage of UV light. For example, tank body 30 may be of opaque, metal or coloured transparent materials.

The fitting end seals onto the tank body and contains any fluid within the chamber until the vapor tank is installed in an appropriate device that is configured to release fluid therefrom. Fitting end 32 is configured for installation in a vaporizer, for example, including threads 38a or another connection. Fitting end 32 further includes a gland 38b or other configuration through which fluid can pass, once the gland is mounted on an appropriate fluid receiver. However, fitting end seals against leakage out of the tank body and is further configured to reduce gas transmission to and from the tank body, to thereby reduce the risk of oxidation.

The vaporizable solution 40 of the present invention is contained, for example sealed, within the chamber.

The vapor tank may be contained with a package and the package may contain instructions for use.

In one embodiment the vaporizable solution may be heated to provide a vapor containing active cannabinoids. The vaporized solution may have a reduced incidence of carcinogens over ingesting smoke from cannabis. The preloaded vapor tank may be purchased by an individual. The preloaded vapor tank may contain a pre-mixed and homogeneous solution with a known, specified concentration of cannabinoids that may be installed in a vaporizer and readily used for the administration of cannabis by inhalation of the resulting vapor.

Example 1—Method for Producing Cannabis Distillate take a measured amount of crude cannabis extract, and dissolve it in an ethanol solvent, 10 ml solvent per 1 gram of extract;
heat the mixture to 45° C. and stir to dissolve fully;
remove from heat, pour into a freezer safe container and freeze in a laboratory freezer, at a temperature range of −20° C. to −40° C., for 24 hours;
remove container from freezer, filter with coarse filter paper first and then with fine filter paper;
re-freeze solution for another 24 hours to precipitate final fats and waxes;
remove solvent in a rotary evaporator under reduced pressure and collect the oil in a 2-neck 2-litre round bottom flask;

install the short path distillation head and a temperature probe into each of the glass joints;

install the distillation receiver in the short path outlet and connect a flask to the distillation receiver;

distillation is carried out by removing about 40% of the atmosphere in the flask and slowly raising the temperature, any fraction isolated below 200° C. are waste and non-useful product;

change the receiving flasks when they are close to filling up in order to avoid contamination of the desired product;

allow the vacuum pump to pull a "hard" vacuum, with as much vacuum pressure as possible (used Edwards E2M30 pump);

the distillation temperature range from 170° C. to 220° C. yielded a mix of terpenes and other aromatics that thermally decomposed; cannabinoids were present in the fraction collected at a temperature range of 220° C. to 240° C.; and tailing were isolated in the fraction collected at a temperature range of 240° C. to 270° C.;

the cannabis distillate generated at 220° C. to 240° C. was found to be highly refined and tested up to 95% purity of THC or CBD depending on cannabis starting material; and the cannabinoid in the distillate was fully decarboxylated, for example, there was a full conversion of THCA to THC.

Example 2: Method for Producing Cannabis Solution Using a Cannabis Distillate

Total THC needed=(grams THC per bottle/ml per bottle)*total volume (ml)$D=(G/M)*V$   DOSING FORMULA Cannabis distillate:PEG 400=1:1 ratio   MIXING FORMULA Considerations:

Determine the total volume of cannabis solution to be made: In order to make 1000 ml of cannabis solution, target 900 ml of total solution so that 10% total volume of the solution is reserved for the addition of the flavoring. Each bottle of cannabis solution is 30 ml and we want to have a dose of 600 mg/bottle thus need to determine the mg/ml ratio and multiply by 30 to get to target dosage.

600 mg THC/30 ml=0.6/30=0.02 mg/ml THC 0.02*1000 ml=20 grams THC.

For a cannabis distillate, 1 g/ml is the average density.

PEG 400 used as a stabilizer in equal proportions to THC.

Procedure:

Mix 20 grams PEG 400 with 20 grams of the distillate (+/–weight correction %), heat and stir until dissolved;

Pour the mixture into a 2000 ml beaker, and add 860 ml of PG to top up the solution to 900 ml;

Heat and stir solution until fully mixed, observe for particulate matter;

If any separation or precipitation is observed, then filter the solution over a bed of packed cotton wool to remove any solid impurities from the solution;

Mix in 100 ml of flavoring into the solution, solution may go cloudy for a few seconds, but clears up when properly mixed; and Pour cannabis solution into packaging.

Example 3: Shelf-Life

The shelf-life testing of solutions prepared according to Examples 1 and 2 showed that the cannabis solution risked degradation under UV light and oxygen exposure.

In order to address UV light degradation, the present invention was packaged in an amber glass vial. The solution proved to be stable with no separation in the amber glass vial for 4 months, at a temperature range from 10° C. to 25° C. Under 5° C. the solution turned slightly cloudy. However, once the solution was warmed above 5° C., it returned to a homogenous, clear state.

When exposed to oxygen and UV light, a color change was observed, whereby the golden solution changed to a red solution (suggesting a higher CBN concentration due to the degradation of THC). Regardless the red solution remained homogenous.

The present invention was also heat stable. The solution remained homogeneous at 80° C. with no observable separation.

The previous description of the disclosed embodiments is provided to enable any person skilled in the art to make or use the present invention. Various modifications to those embodiments will be readily apparent to those skilled in the art, and the generic principles defined herein may be applied to other embodiments within the claims. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims. For US patent properties, it is noted that no claim element is to be construed under the provisions of 35 USC 112, sixth paragraph, unless the element is expressly recited using the phrase "means for" or "step for".

We claim:

1. A pre-packaged cannabis vape cartridge consisting essentially of:

a) a sealable liquid container;

b) a cannabinoid distillate of tetrahydrocannabinol or cannabidiol condensed from vapors of a solvent extract of cannabis at a vapor temperature in the range of 220° C. to 240° C. under a vacuum in the range of 0.1 TORR to 0.3 TORR;

c) polyethylene glycol; and d) propylene glycol, wherein the cannabis distillate is free of terpenes, is fully decarboxylated and contains no tetrahydrocannabinol acid or cannabidiol acid and wherein the sealable liquid container is a vapor tank consisting essentially of a tank body, an inner chamber, and a fitting end with a gland.

2. The pre-packaged cannabis vape cartridge of claim 1, wherein the polyethylene glycol is in a ratio of 3:1 to 1:1 of the polyethylene glycol to the cannabinoid distillate, respectively.

3. The pre-packaged cannabis vape cartridge of claim 1, wherein the propylene glycol is in a ratio of 200:1 to 1:1 of the propylene glycol to a total volume of the polyethylene glycol and the cannabinoid distillate, respectively.

4. A pre-packaged cannabis vape cartridge consisting essentially of:

a) a sealable liquid container;

b) a cannabinoid distillate of tetrahydrocannabinol or cannabidiol condensed from vapors of a solvent extract of cannabis at a vapor temperature in the range of 220° C. to 240° C. under a vacuum in the range of 0.1 TORR to 0.3 TORR;
c) polyethylene glycol;
d) propylene glycol; and
e) a flavoring, wherein the cannabis distillate is free of terpenes, is fully decarboxylated and contains no tetrahydrocannabinol acid or cannabidiol acid and wherein the sealable liquid container is a vapor tank consisting essentially of a tank body, an inner chamber, and a fitting end with a gland.

5. The pre-packaged cannabis vape cartridge of claim 4, wherein the polyethylene glycol is in a ratio of 3:1 to 1:1 of the polyethylene glycol to the cannabinoid distillate, respectively.

6. The pre-packaged cannabis vape cartridge of claim 4, wherein the propylene glycol is in a ratio of 200:1 to 1:1 of the propylene glycol to a total volume of the polyethylene glycol and the cannabinoid distillate, respectively.

\* \* \* \* \*